(12) United States Patent
Amborn et al.

(10) Patent No.: US 7,967,773 B2
(45) Date of Patent: Jun. 28, 2011

(54) TWO PIECE MEDICATION CASSETTE CLOSURE APPARATUS AND METHOD

(75) Inventors: Chad Amborn, Minneapolis, MN (US); Chris Lacy, Arden Hills, MN (US); Steven Cote, Stillwater, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 0 days.

(21) Appl. No.: 12/578,128

(22) Filed: Oct. 13, 2009

(65) Prior Publication Data

US 2011/0087165 A1  Apr. 14, 2011

(51) Int. Cl.
*A61N 1/30* (2006.01)
*F04B 43/08* (2006.01)

(52) U.S. Cl. ...................... 604/19; 417/477.2

(58) Field of Classification Search ............ 206/807, 206/1.5; 417/477.1–477.14; 604/110, 111, 604/29; 220/324, 322, 315, 796; 215/280, 215/273; 70/57, 57.1, 58, 63; 222/105, 131, 222/183; 251/367
See application file for complete search history.

(56) References Cited

U.S. PATENT DOCUMENTS

| | | | |
|---|---|---|---|
| 3,494,458 A | 2/1970 | Meierhoefer | |
| 4,381,836 A | 5/1983 | Rivkin et al. | |
| 4,451,693 A | 5/1984 | Vest | |
| 4,559,038 A | 12/1985 | Berg et al. | |
| 4,565,542 A | 1/1986 | Berg | |
| 4,567,983 A | 2/1986 | Morris | |
| 4,634,004 A | 1/1987 | Mortensen | |
| 4,650,469 A | 3/1987 | Berg | |
| 4,802,601 A * | 2/1989 | Pijanowski et al. | 220/4.01 |
| 4,867,738 A * | 9/1989 | Mintz | 604/6.15 |
| D309,662 S | 7/1990 | Gorton | |
| 5,106,366 A * | 4/1992 | Steppe | 604/30 |
| 5,336,190 A | 8/1994 | Moss et al. | |
| 5,370,622 A | 12/1994 | Livingston et al. | |
| 5,397,222 A * | 3/1995 | Moss et al. | 417/477.2 |
| 5,429,485 A | 7/1995 | Dodge | |
| 5,482,446 A | 1/1996 | Williamson et al. | |
| 5,531,697 A | 7/1996 | Olsen | |
| 5,531,698 A | 7/1996 | Olsen | |
| 5,564,915 A | 10/1996 | Johnson | |
| D376,848 S | 12/1996 | Zeilig et al. | |
| 5,647,854 A | 7/1997 | Olsen | |
| 5,658,252 A * | 8/1997 | Johnson | 604/131 |
| 5,695,473 A | 12/1997 | Olsen | |
| 5,755,691 A | 5/1998 | Hilborne | |
| 5,772,409 A | 6/1998 | Johnson | |
| 5,782,805 A | 7/1998 | Meinzer et al. | |
| 5,788,671 A | 8/1998 | Johnson | |

(Continued)

*Primary Examiner* — Nicholas D Lucchesi
*Assistant Examiner* — Jenna Zhang
(74) *Attorney, Agent, or Firm* — Patterson Thuente Christensen Pedersen, P.A.

(57) ABSTRACT

A disposable medical cassette apparatus and method for housing medication in a tamper resistant enclosure for selective coupled attachment to an ambulatory infusion pump. In some embodiments, the device may include a first assembly comprising a rear housing and a pressure plate affixed to one another, as well as a second assembly comprising a cover that includes a plurality of lock feature protrusions and at least one slotted aperture. The first assembly and second assembly are adapted for permanent coupling by a first and second lock arrangements. Generally, the first lock arrangement includes lock feature protrusions of the second assembly engaging within the lock receiving structures of the first assembly. Further, the second lock arrangement includes at least one tabbed snap member of the first assembly engaging within at least one corresponding slotted aperture of the second assembly.

19 Claims, 13 Drawing Sheets

U.S. PATENT DOCUMENTS

| | | |
|---|---|---|
| 5,823,746 A | 10/1998 | Johnson |
| 5,928,196 A | 7/1999 | Johnson et al. |
| 5,935,099 A | 8/1999 | Peterson |
| 5,954,485 A | 9/1999 | Johnson |
| 5,993,420 A | 11/1999 | Hyman et al. |
| 6,056,522 A | 5/2000 | Johnson |
| 6,059,753 A | 5/2000 | Faust et al. |
| 6,077,055 A | 6/2000 | Vilks |
| 6,123,686 A | 9/2000 | Olsen |
| 6,131,773 A | 10/2000 | Wade et al. |
| 6,202,708 B1 | 3/2001 | Bynum |
| D447,558 S | 9/2001 | Cartledge et al. |
| 6,374,876 B2 | 4/2002 | Bynum |
| 6,422,057 B1 | 7/2002 | Anderson |
| 6,475,180 B2 | 11/2002 | Peterson |
| 6,742,992 B2 | 6/2004 | Davis |
| 7,150,735 B2 | 12/2006 | Hickle |
| 7,258,534 B2 | 8/2007 | Fathallah et al. |
| 7,347,836 B2 | 3/2008 | Peterson |
| 7,654,976 B2 | 2/2010 | Peterson |
| 2008/0065007 A1 | 3/2008 | Peterson |
| 2008/0065016 A1 | 3/2008 | Peterson |
| 2008/0275425 A1 | 11/2008 | Strickler et al. |
| 2010/0094224 A1 | 4/2010 | Fathallah et al. |

\* cited by examiner

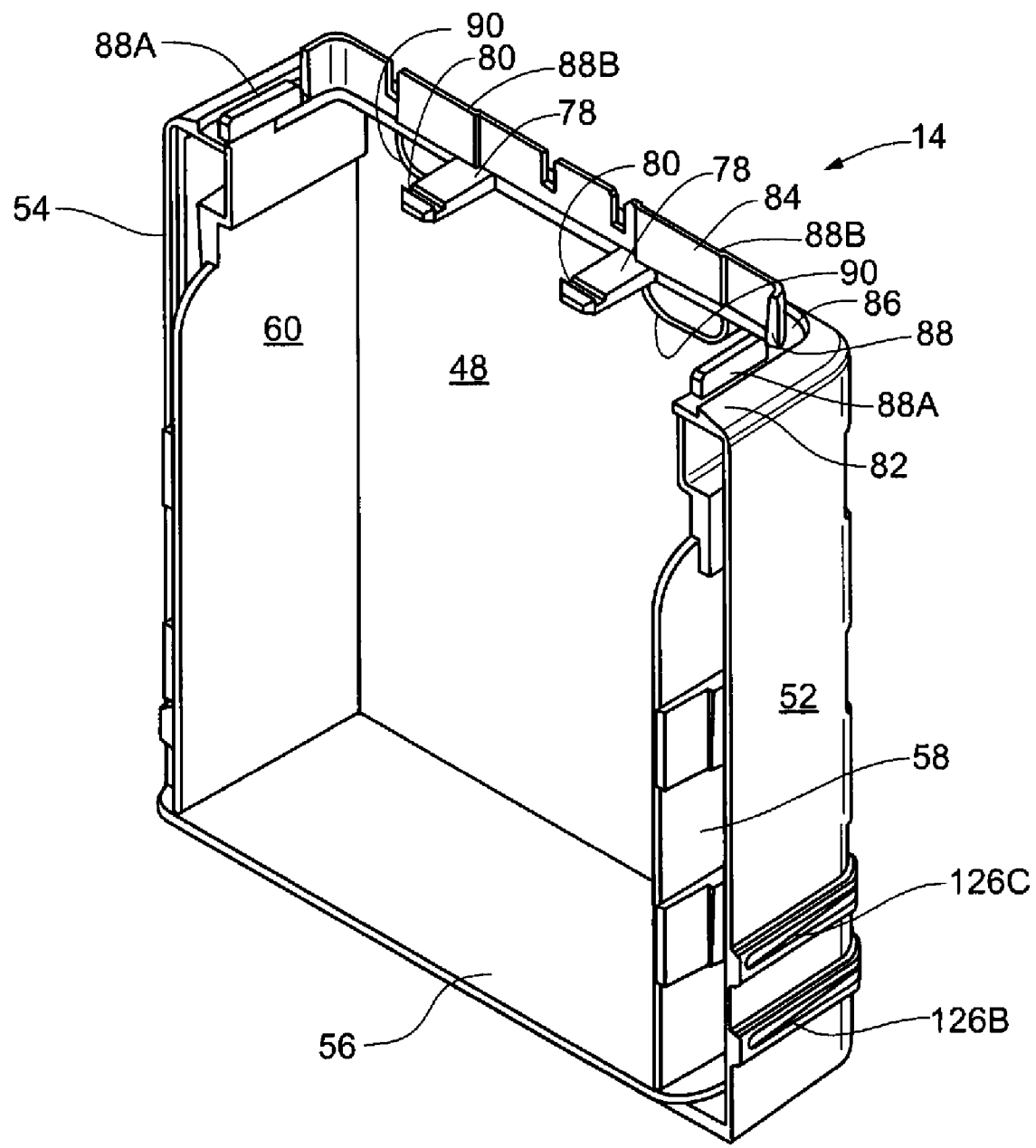

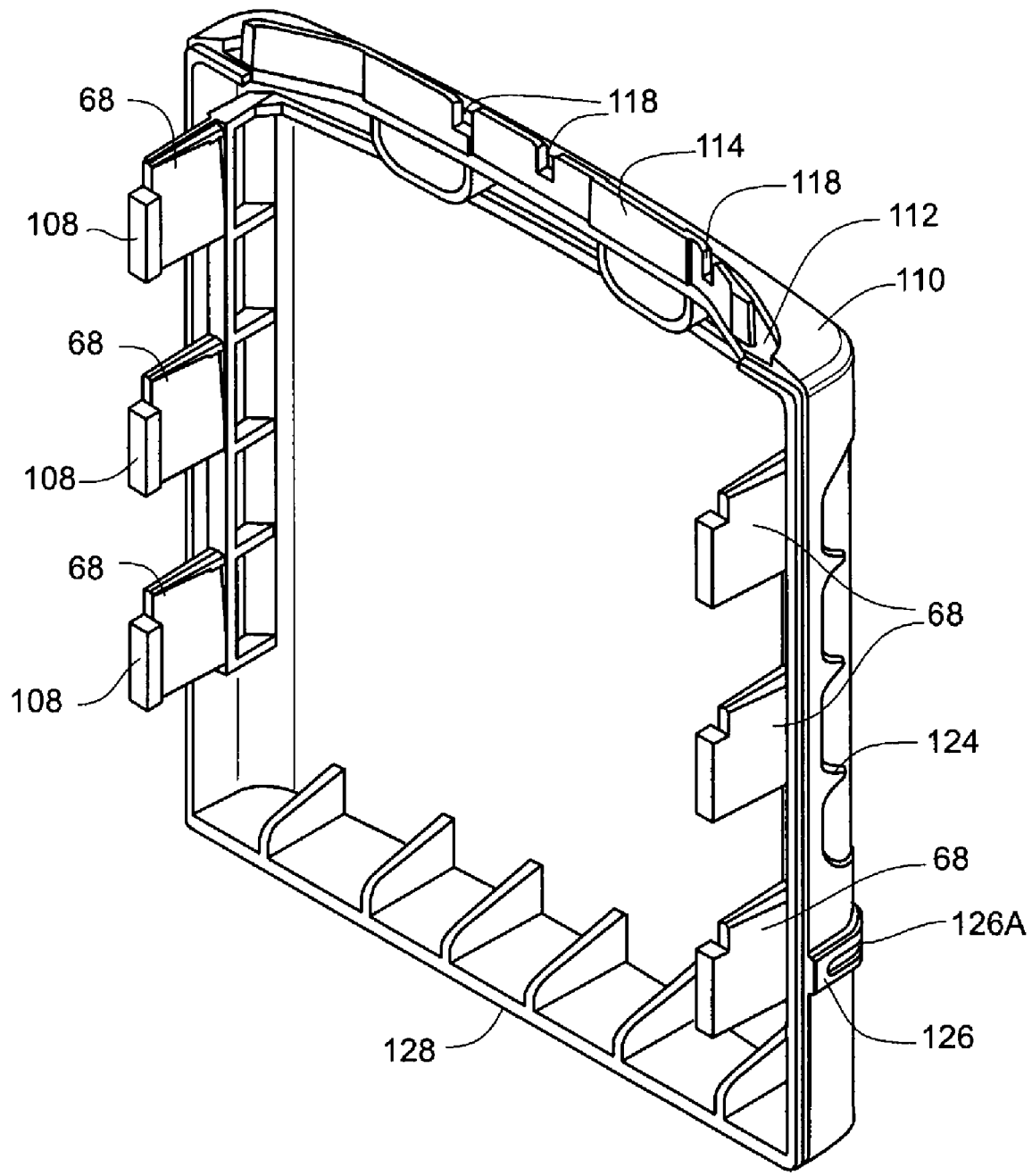

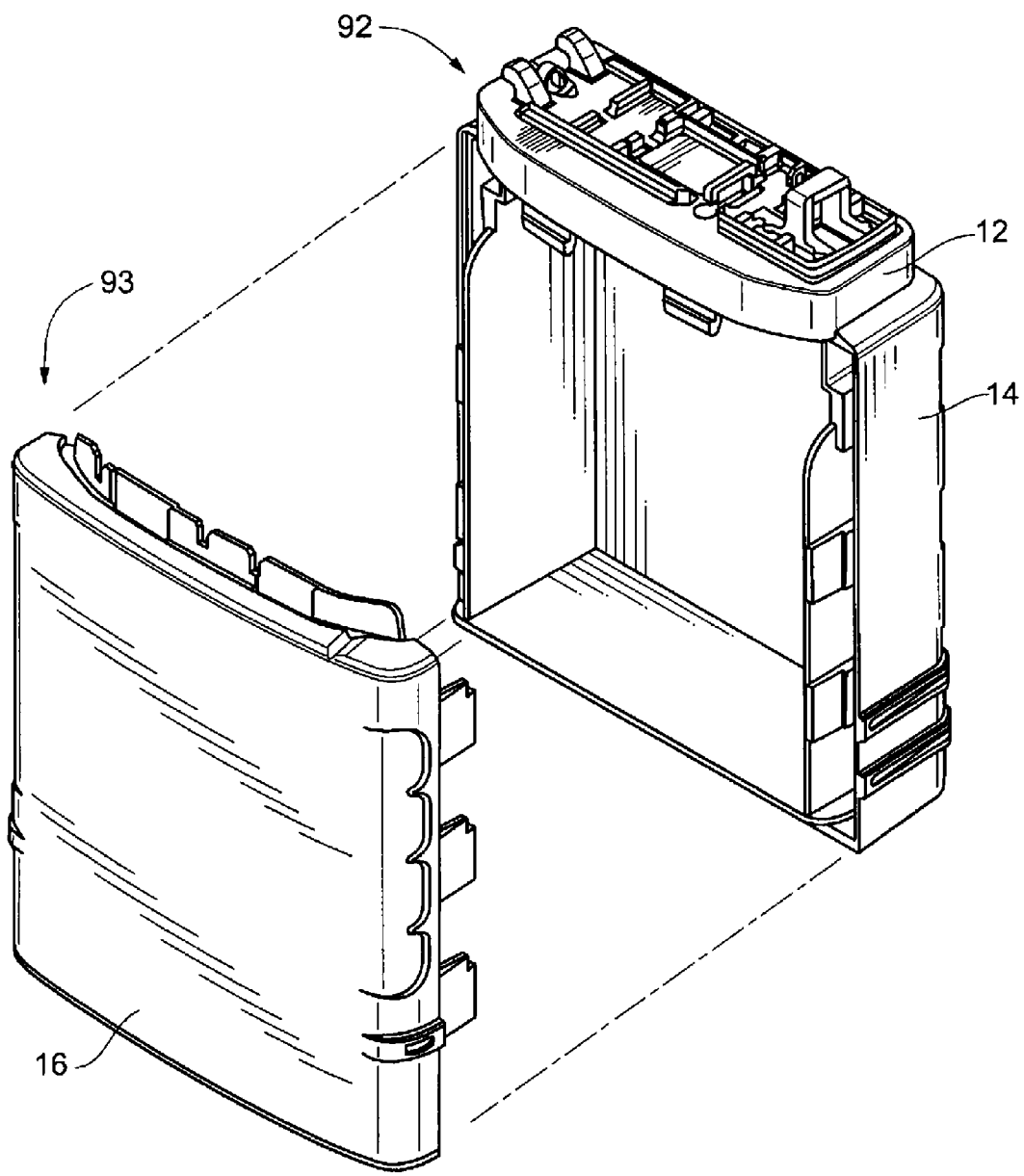

TWO PIECE MEDICATION CASSETTE CLOSURE APPARATUS AND METHOD

FIELD OF THE INVENTION

The present invention relates to medical device housings for securing medication in an enclosure. More particularly, the present invention relates to a cassette enclosure for housing medication in a tamper resistant structure adapted for use with an ambulatory peristaltic infusion pump and methods thereof.

BACKGROUND OF THE INVENTION

Tamper-proof and tamper-resistant containers for housing medication have been designed for various types of medical equipment and applications. Such past medical containers were of all sizes and shapes and were created for patient protection and safety among other reasons. Accordingly, products in the medical field which limit easy intentional or unintentional access to potentially harmful substances are desirable as they help to preserve a variety of healthcare expectations with respect to handling medication safely. In the drug delivery field, such safety considerations have been sometimes referred to as the five rights of medication safety, that is, right patient, right drug, right dose, right route, and right time. Devices which can help maintain control over access to medication once it enters a patient environment are accordingly important tools in attempts to preserve many of these rights.

One specific area in which such secure medication housings have been useful was in the context of infusion pumps, and more particularly, ambulatory infusion pumps. In the past, some ambulatory infusion pumps have used cassette attachments containing bag reservoirs of medication as the source of medication for administration to patients. In general, most of these cassette designs were small enclosures that housed only a limited amount of medication. Often these cassettes were simply one piece devices that were ultrasonically sealed at manufacture. Some of these cassettes provided characteristics of readily portable containers capable of protecting a reservoir of medication, as well as providing an interface which could be quickly recognized by and secured in an operable fashion to an infusion pump.

Despite the advantages of past cassettes, the design of these types of cassettes caused them to be unsuitable to use in various situations. For example, some treatments required larger amounts of medication to be available than could be housed in existing cassettes. In such cases, multiple cassettes were necessary. Further, additional starting and stopping of treatment was required. These limitations were undesirable and inconvenient in many circumstances. Moreover, these designs did not lend themselves easily to a simple enlargement of the cassettes as similarly configured cassettes would require large cumbersome devices.

Further, a frequent issue in past cassette designs was the difficulty pharmacists had removing air bubbles from medication bags fitted within previously sealed cassettes. Specifically, air bubbles were difficult to remove in many past cassette designs because the medication bags were located in ultrasonically sealed cassettes that could not be directly accessed when filled. Accordingly, removing air bubbles once inside the cassette was not easy as the entire cassette and bag would need to be shaken, tapped or jolted.

Therefore, what is needed is an enclosure device which overcomes the deficiencies of the past, and which enables a medication cassette that may be coupled to a peristaltic ambulatory infusion pump and which can house a large amount of medication. Further, although a tamper resistant enclosure is desired when the device is used by patients, it is also desired for the enclosure to allow easy access by a pharmacist for filling with medication and removing air bubbles from the reservoir prior to patient use.

SUMMARY OF THE INVENTION

The present invention overcomes the problems of the prior art by providing an improved method and device to achieve a secure cassette assembly for use with an ambulatory infusion pump. A device is provided which makes use of a multi-piece housing that is tamper resistant and lends itself to improved medication administration.

In one embodiment, a disposable medical cassette is disclosed for housing medication in a tamper resistant enclosure for selective coupled attachment to an ambulatory infusion pump. This cassette includes a first assembly comprising a rear housing and a pressure plate secured to one another. The first assembly also includes a plurality of tamper resistant lock receiving structures integrally formed in the rear housing in spaced apart relation about a perimeter of the first assembly and at least one tabbed snap member. The embodiment further includes a second assembly including a cover with a plurality of lock feature protrusions and at least one slotted aperture. In this embodiment, the first assembly and second assembly are adapted for permanent coupling by a first lock arrangement and a second lock arrangement. Also, the first lock arrangement includes the lock feature protrusions of the second assembly configured to engage with the lock receiving structures of the first assembly. Further, the second lock arrangement includes at least one tabbed snap member of the first assembly configured to engage with at least one corresponding slotted aperture of the second assembly.

In another embodiment according to the present invention, a disposable medical cassette for housing medication in a tamper resistant enclosure for selective coupled attachment to an ambulatory infusion pump is included. The cassette includes a cover member having a perimeter adapted for coupling. The cassette further includes a rear assembly comprising a top pressure plate and a partial housing structure having a set of outer walls and a set of inner walls. The outer walls define a perimeter for coupled engagement to the perimeter of the cover such that a seam is formed between the rear housing and the cover. Also, the inner walls extend in a generally parallel manner to the outer walls. The inner walls further have a height greater than the outer wall and form a barrier located beneath the seam.

According to an embodiment of the present invention, a disposable medical cassette for coupled attachment to an ambulatory infusion pump for housing medication includes a multi-piece assembly comprising two interlocking pieces designed for tool-less manual assembly to secure a reservoir of medication. The disposable medical cassette has a tamper resistant configuration having at least one snap and aperture lock assembly for holding the two interlocking pieces together. The snap and aperture lock assembly is not accessible without deforming or compromising the cassette once assembled. Also, the assembled disposable medical cassette provides an interior chamber for housing the reservoir of medication.

In another embodiment according to the present invention, a method for assembling a medication cassette is disclosed. The method includes obtaining a first assembly and a second assembly adapted for permanent coupling and housing a medication reservoir for an ambulatory infusion pump. The first assembly including a pressure plate and rear housing having tabbed snaps projecting from the pressure plate and a plurality of receiving members located along the sides of the rear housing such that the receiving members are spaced apart by a plurality of recesses. The second assembly includes a cover with a plurality of slotted apertures and a plurality of lock members. The method further includes filling a medication bag and placing the medication bag within the first assembly. The method also includes placing the lock members of the second assembly into spaced apart recesses of the first assembly. Finally, the method also includes sliding the lock members of the second assembly into the receiving members of the first assembly while engaging the tabbed snaps of the first assembly into the slotted apertures of the second assembly.

Yet another embodiment includes a method for assembling a medication cassette by providing instructions for medication cassette assembly. The instruction steps include obtaining a first assembly and a second assembly adapted for permanent coupling and housing a medication reservoir for an ambulatory infusion pump. The first assembly includes a pressure plate and rear housing having tabbed snaps projecting from the pressure plate and a plurality of receiving members located along the sides of the rear housing such that the receiving members are spaced apart by a plurality of recesses. The second assembly includes a cover with a plurality of slotted apertures and a plurality of lock members. The instructions further include filling a medication bag and placing the medication bag within the first assembly. The instructions also include placing the lock members of the second assembly into spaced apart recesses of the first assembly. Finally, the instructions include sliding the lock members of the second assembly into the receiving members of the first assembly while engaging the tabbed snaps of the first assembly into the slotted apertures of the second assembly.

BRIEF DESCRIPTION OF THE DRAWINGS

The invention may be more completely understood in consideration of the following detailed description of various embodiments of the invention in connection with the accompanying drawings, in which:

FIG. 5B illustrates generally a top corner perspective view of a rear housing of a medication cassette enclosure according to an embodiment of the invention.

FIG. 6B illustrates generally a rear corner perspective view of a cover of a medication cassette enclosure according to an embodiment of the invention.

FIG. 7 illustrates an unassembled perspective view of a medication cassette according to an embodiment of the invention.

DETAILED DESCRIPTION OF THE DRAWINGS

The invention may be embodied in other specific forms without departing from the essential attributes thereof, therefore, the illustrated embodiments should be considered in all respects as illustrative and not restrictive.

In various embodiments of this invention an apparatus comprising a medical cassette for ambulatory use is shown. Embodiments disclosed generally are directed to medication cassettes that may be coupled to peristaltic ambulatory infusion pumps. The cassette generally comprises a multiple piece design that can be quickly assembled by engaging the pieces using a combination of lock arrangements. The locking configuration includes an easy to use design having multiple locking arrangements including a first lock arrangement having a plurality of lock members and a second lock arrangement utilizing tabbed snaps and apertures.

Cassettes embodiments are generally further adapted to securely house relatively large bags of medication, for example, bags containing at least 250 ml of medication, in a central compartment. However, smaller medication bags and housing components are also contemplated by this disclosure. In various embodiments this compartment may be surrounded by a set of interior walls and a set of exterior walls. Further, the enclosure is impact resistant due to its structural design and material composition. Embodiments further include an assembly where a pharmacist is permitted to access the interior of the cassette after manufacture for filling the cassette with medication and for removing air bubbles from the medication bag. The configuration also allows the pharmacist to close the cassette into a tamper proof configuration without the need for tools.

Figure 1:
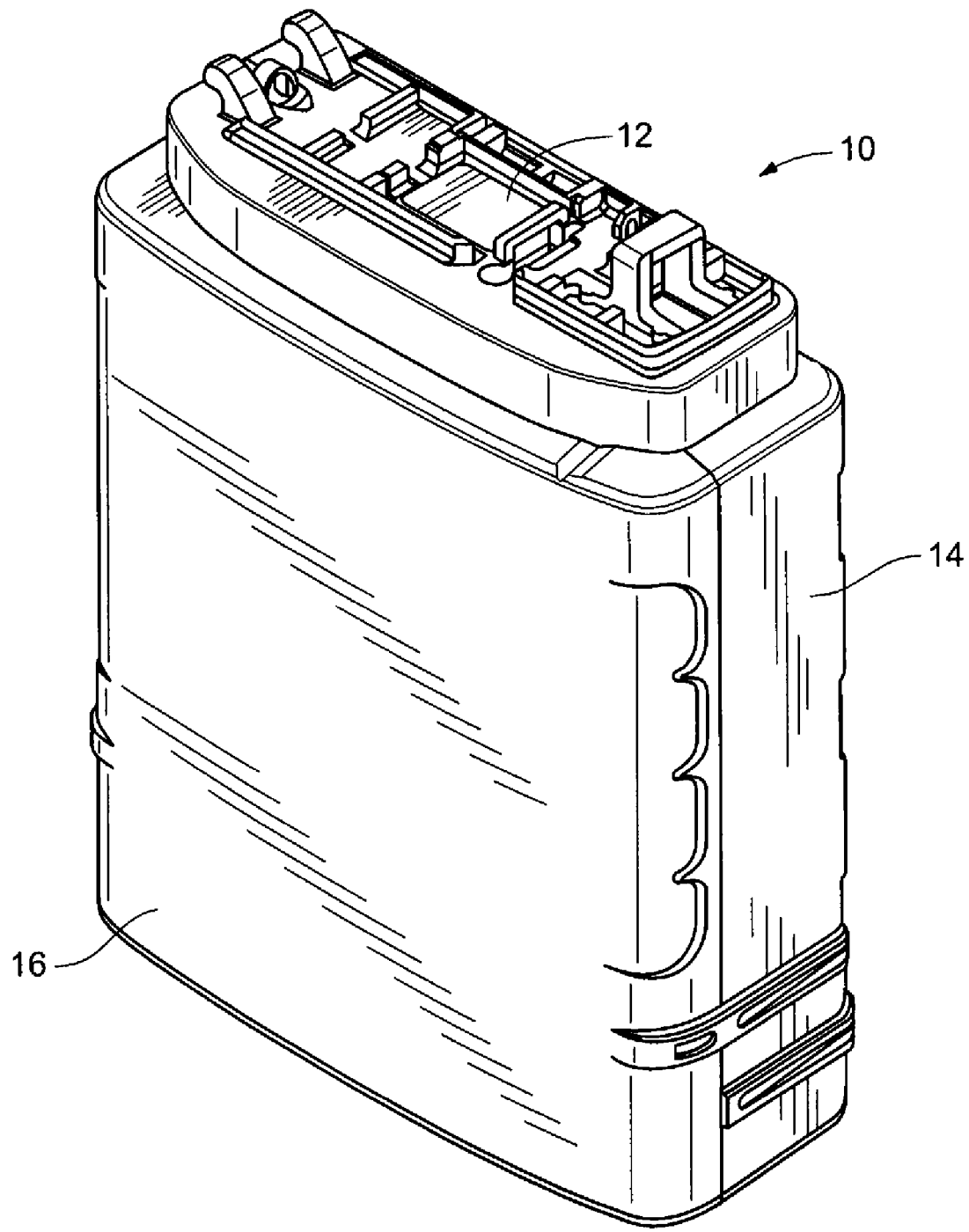
FIG. 1 illustrates generally a medication cassette enclosure for use with an ambulatory infusion pump according to an embodiment of the invention.

FIG. 1 discloses an assembled cassette 10 for use with an ambulatory infusion pump. The cassette assembly 10 generally includes a pressure plate 12, a rear housing 14 and a cover member 16. The cassette 10 is designed such that it is compatible with an ambulatory infusion pump having a lower surface that can readily engage with the top pressure plate 12 of the cassette 10. Further, the cassette 10 is designed so that the attached infusion pump can pump medication out through a tubing (not shown) that extends from the cassette to a patient. Specifically, the tubing extends from a centrally enclosed medication bag across the top face of the pressure plate 12 of the device before traveling to the patient. The cassette 10 further contains a significant amount of medication volume but remains amenable to hand-held dimensions. In some cases, this medication volume may be 250 ml of medication, however, larger or smaller volumes are contemplated by this design.

Figure 2:
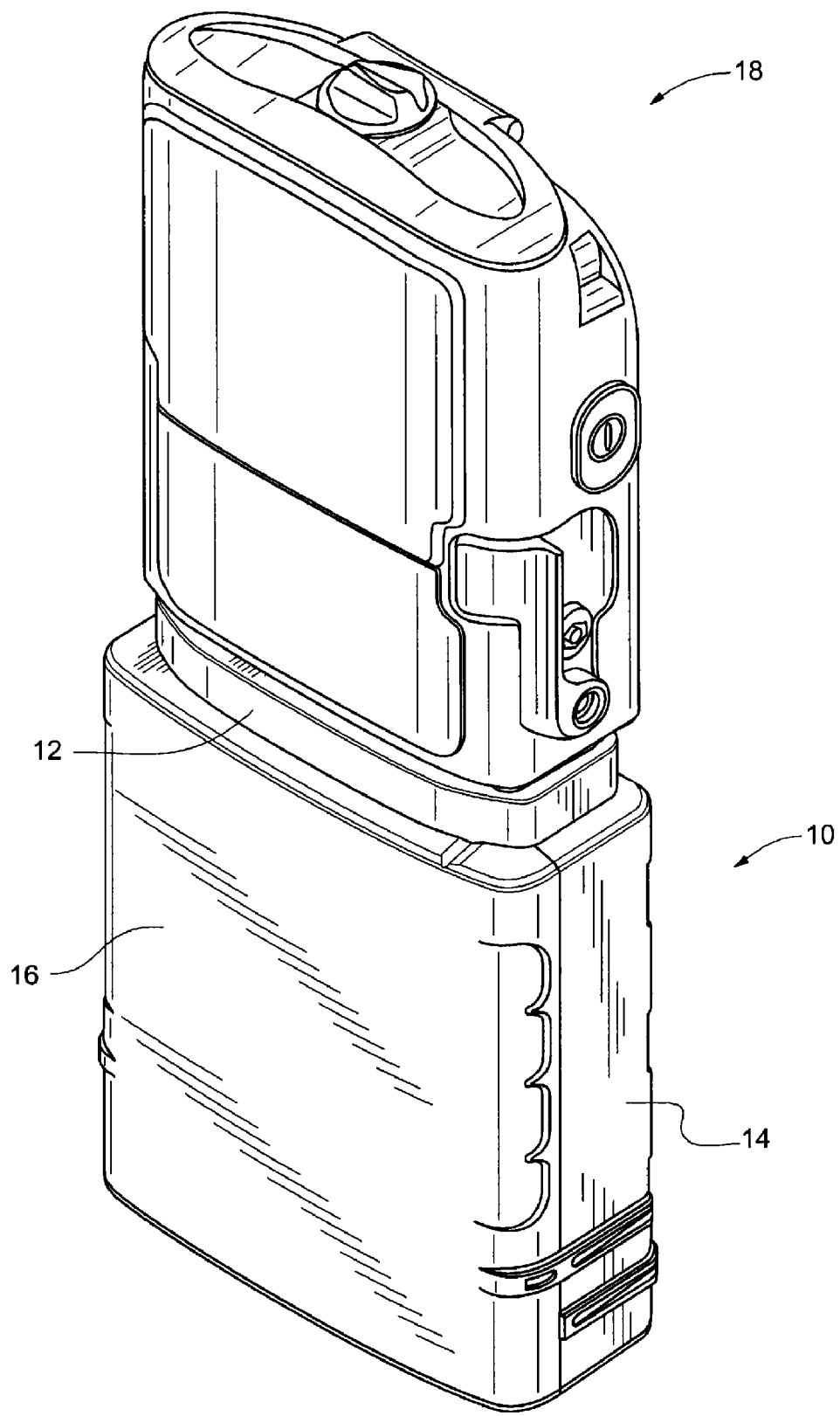
FIG. 2 illustrates generally a medication cassette enclosure coupled to an ambulatory infusion pump according to an embodiment of the invention.

Referring now to FIG. 2, a cassette assembly 10 is shown attached to an ambulatory infusion pump 18. As shown, the medication cassette assembly 10 is coupled in a removable manner such that the reservoir of medication is located directly below the peristaltic infusion pump 18 used to deliver the medication. Medication is delivered through a tube extending out of the top of the cassette 10 and is held in place by guide members formed in the pressure plate 12. The tubing in the pressure plate 12 and the opening to the interior of the cassette 10 is concealed from view or direct access when the cassette 10 is attached to the pump 18. Typically, tubing supplying medication would exit the left side of the pressure plate 12, however, the exposed exiting medication tube is not shown from the view of FIG. 2.

Figure 3:
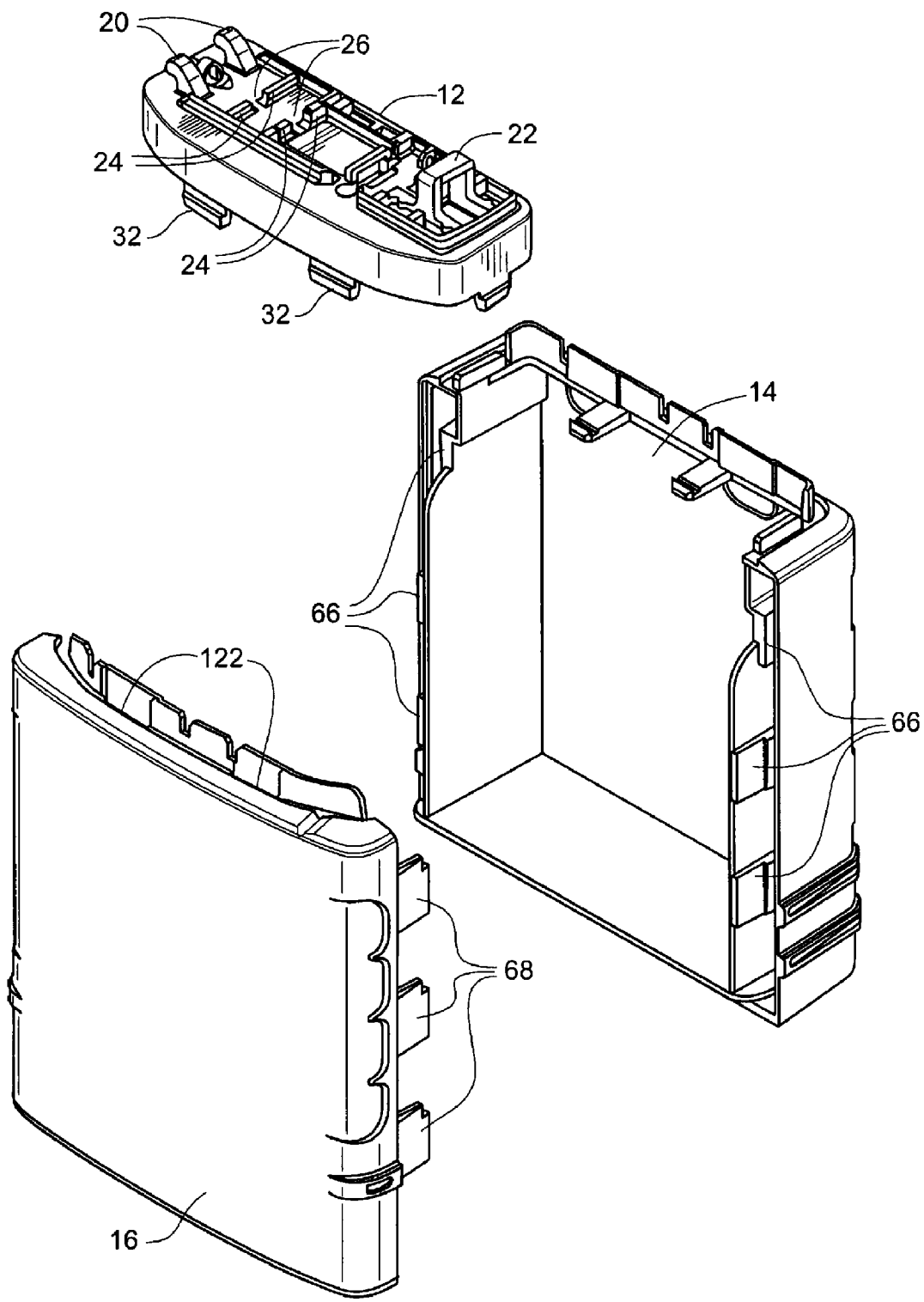
FIG. 3 illustrates generally an exploded view of a medication cassette enclosure according to an embodiment of the invention.
Figure 4A:
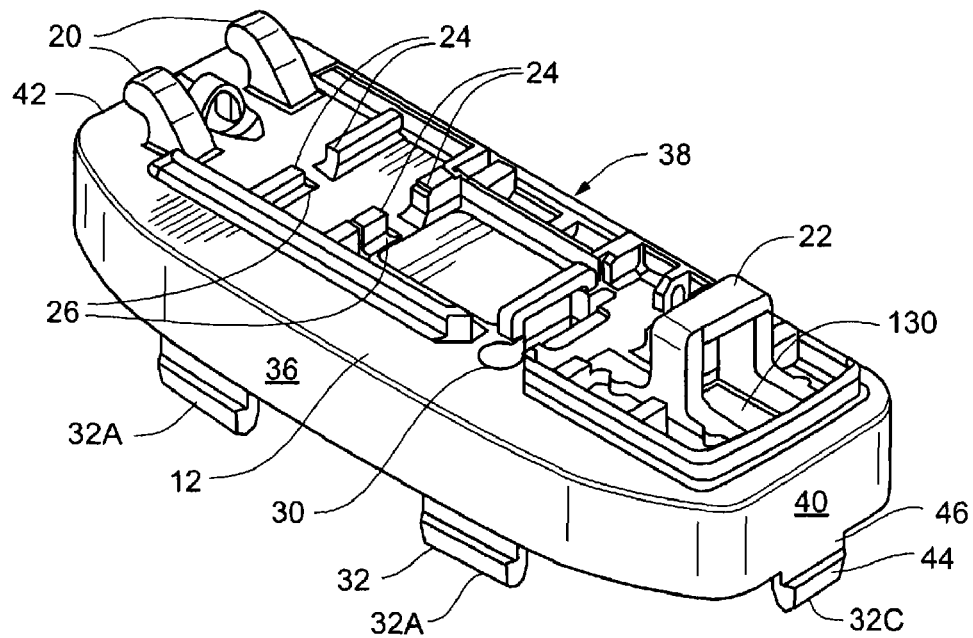
FIG. 4A illustrates generally a top corner perspective view of a pressure plate of a medication cassette enclosure according to an embodiment of the invention.
Figure 4B:
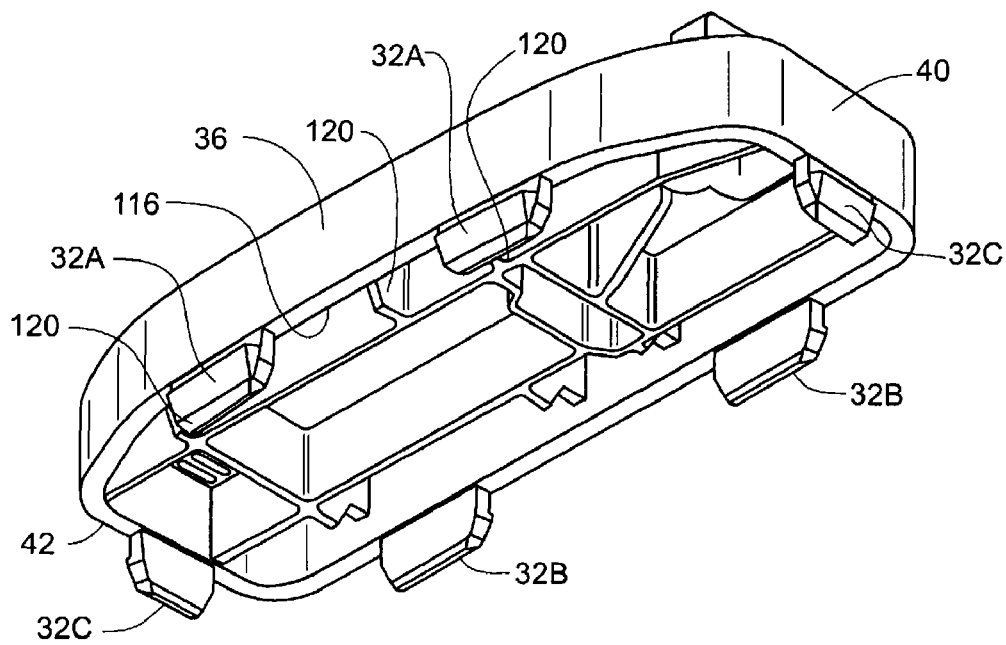
FIG. 4B illustrates generally a bottom corner perspective view of a pressure plate of a medication cassette enclosure according to an embodiment of the invention.

The cassette assembly 10 is shown in an exploded view in FIG. 3. Accordingly, the three primary features which lock together to form a secure enclosure are set forth, namely the pressure plate 12, the rear housing 14, and the cover member 16. In general, the pressure plate contains features which provide compatibility and operational coupling to the pump 12, as can be seen also in FIGS. 4A and 4B. These features include a pair of hooks 20 at one end of the pressure plate 12 and a latch arch 22 at the opposite end. Further, guide members 24 on the surface of the pressure plate 12 provide a series of central passageways 26 for a medication tube to reside. The pressure plate design disclosed differs from past pressure plate structures and designs. For example, the design of the lower half of the pressure plate 12 now contains a plurality of protrusions and assembly features.

As mentioned, the bottom half of the pressure plate 12 includes a number of pressure plate tabbed snaps 32 spaced around the lower perimeter of the pressure plate 12. Specifically, in FIGS. 4A and 4B six tabbed snaps are disclosed. There are two snaps 32A located in the front side 36 of the pressure plate 12, two snaps 32B located along the back side 38 of the pressure plate 12, and a single snap 32C found on each of the right and left sides 40 and 42 of the pressure plate 12. The snaps 32 each comprise elongated projections extending from the lower surface of the pressure plate 12. The projections each include an angled outer face 44 forming a wedge shape with an upper planar base portion 46. In general, the pressure plate 12 and its snaps 32 are comprised of polycarbonate material which is fairly rigid and has limited flexibility.

Figure 5A:
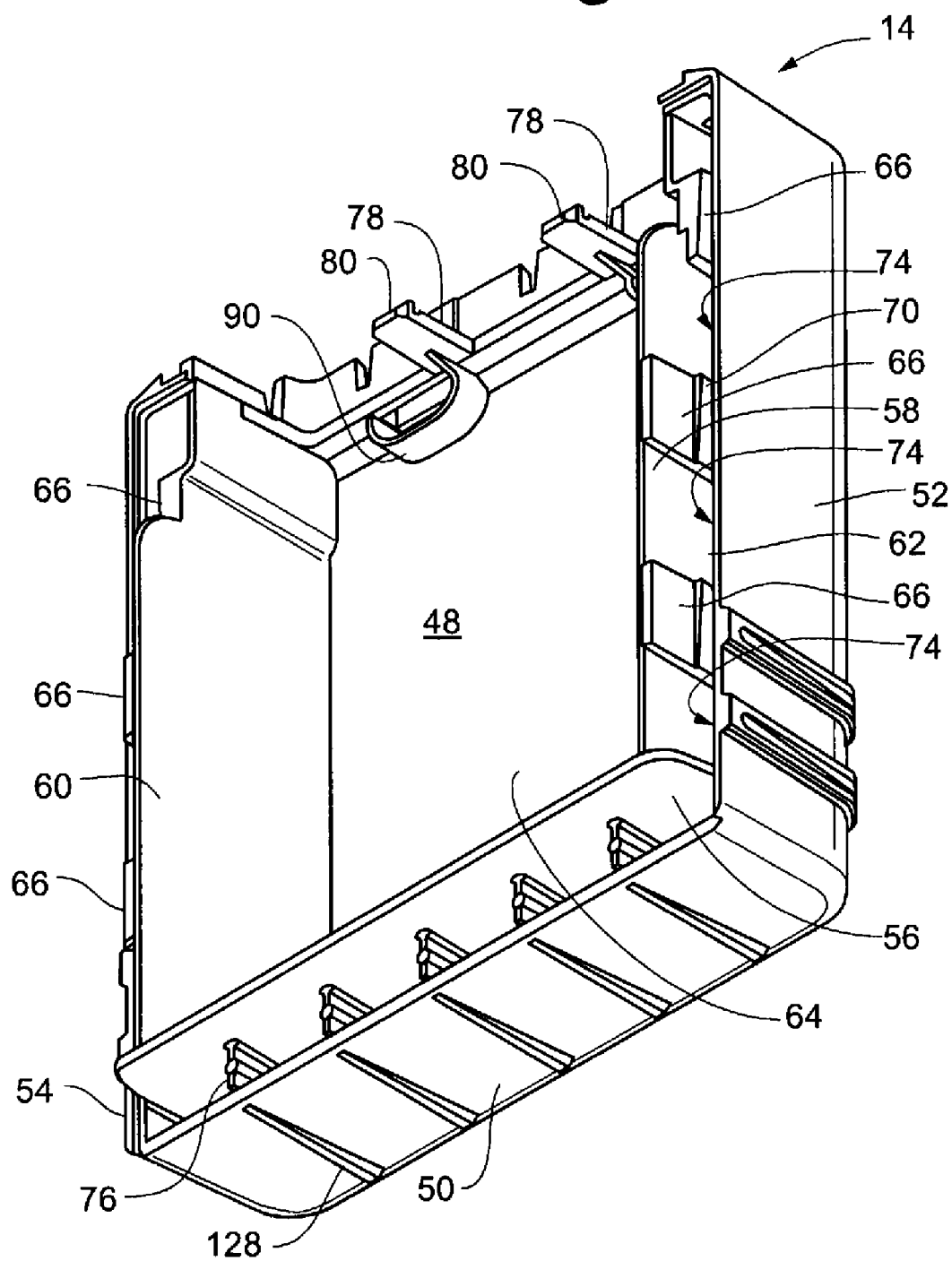
FIG. 5A illustrates generally a bottom corner perspective view of a rear housing of a medication cassette enclosure according to an embodiment of the invention.

The rear housing 14 is seen in FIG. 5. The rear housing 14 is a molded plastic member generally made up of propylene material. The housing is accordingly, somewhat flexible and durable as the shape and type of material generally make the housing impact-resistant. The rear housing 14 comprises the rear wall 48 of the cassette 10 as well as a partial bottom wall 50 and partial right and left sidewalls 52 and 54. The rear housing 14 further has an additional interior bottom wall 56 and interior sidewalls 58 and 60. These interior walls 56, 58, and 60, are oriented within the outer walls 50, 52, and 54, in a similar orientation and in largely parallel relation to their outer corresponding walls. The interior walls extend further forward from the rear wall 48 than the outer bottom wall 50 and side walls 52 and 54 as one aspect of a tamper resistant enclosure. Specifically, the extended interior housing walls provide a barrier to the interior of the housing from access attempts through the outside seam 62 of the outer housing where the cover and rear member come together. A centrally located, open chamber 64 is therefore provided within the interior sidewalls 58 and 60 and interior bottom wall 56 for protecting a medication bag that is at least partially surrounded by both interior and exterior sets of walls.

Between the two sets of walls are a number of features for assembling the housing, creating stability, and providing tamper-resistant engagement. First, between the interior and exterior sidewalls are six lock receiving members 66 (also referred to as lock receiving structures) that are shaped to cooperate with corresponding lock members 68 (also referred to as lock feature protrusions) that project from the cover 16. The engagement configuration discussed between the lock members 68 and lock recovery members replicate the first of two lock configurations utilized by this design. Each receiving member 66 has a sloped member 70 behind which an undercut space 72 is located. (See FIGS. 9A-C) Further, spaced between each of the receiving members 66 are recesses 74 in which the lock members 68 of the cover 16 may be placed during the initial stage of cassette assembly. Between the interior bottom wall 56 and the outer bottom wall 50 are a plurality of reinforcing webs 76 that provide additional stability between the interior wall 56 and exterior wall 50. Similarly intermediate flange supports 144 provide support between the interior sides 58 and 60 and their respective adjacent walls 52 and 54.

The interior walls 56, 58, and 60 of the rear housing 14 have generally smooth surfaces facing interior chamber 64 to accommodate a large flexible reservoir of medication such that a medication bag can be readily placed inside the interior housing when the cassette 10 is assembled. Two projections 78 do, however, extend forward inside the top interior chamber 64 of the cassette 10. These projections 78 each include a small protrusion at their ends forming a bag hook 80. Accordingly, a bag of medication may be conveniently hooked and secured into place over these two bag hooks 80.

The rear housing 14 also has upper lip 82 of material surrounding the perimeter of the outer walls 48, 52 and 54 as well as a notched projection 84 extending above the lip 82. (See FIG. 5) In general, the upper lip 82 of the housing is a fairly narrow surface of material containing a groove 86 in which the perimeter of the pressure plate 12 corresponds and can be placed during manufacture. Proximate the groove 86 in the upper lip 82 are four slotted apertures 88 in the rear housing member 14. One of these slotted apertures 88A is found on each end of the rear housing 14 and two of these slotted apertures 88B are located at the rear of the housing. These slotted apertures 88 are shaped for receiving the snaps 32 extending from the pressure plate 12. Moreover, barrier flanges 90 surround the areas in which the snaps 32 are to be inserted at the rear wall 48 of the rear housing 14. Accordingly, this extra material provides additional protection to a medication bag located in the interior of the housing.

At manufacture, the pressure plate 12 is affixed to the rear housing 14 to form the first assembly 92 (also referred to as the rear assembly) of the cassette. (See FIG. 7.) The pressure plate 12 and rear housing 14 are affixed together by insertion of the four rear and two side snaps 32 of the pressure plate 12 into the corresponding slotted apertures 88 in the upper lip 82 of the rear housing 14. Once the snaps 32 have been inserted into place within the slotted apertures 88 they are designed such that they are not easily removed without significant force or damage to the cassette.

Figure 6A:
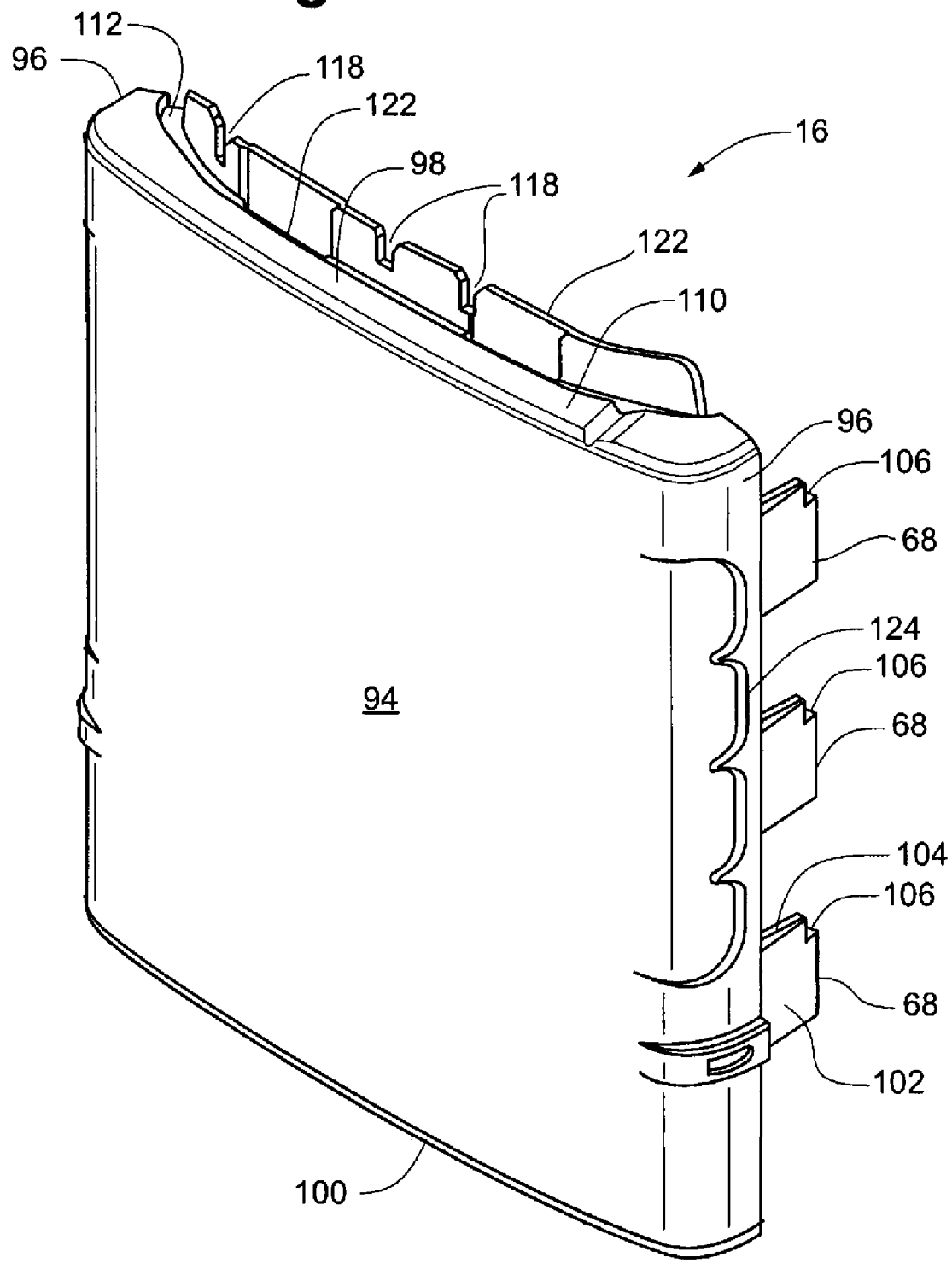
FIG. 6A illustrates generally a front corner perspective view of a cover of a medication cassette enclosure according to an embodiment of the invention.

The cover plate or cover member 16 is shown in FIG. 6. Cover member 16 generally comprises a second assembly 93. The cover member 16 includes the front wall 94 of the cassette assembly as well as partial side, top, and bottom walls 96, 98 and 100, respectively. The surfaces of the side, front, and top members are formed such that the outer surface of the cover member has smooth transitions between these faces.

Six lock members 68 extend from the sides of the cover member 16. These features are located in generally spaced apart relation with one another for distances similar to the spacing of the receiving members 66 of the rear housing 14. The lock members 68 are generally wedge shaped protrusions that have a flat outer surface 102 and angled interior of surface 104. The outwardly projecting ends of the lock members 68 have tips with notches 106 at the top. Additionally, the tips of the lock members 68 contain an additional block of material constituting an undercut tab bar 108. These lock members 68 are sized such that they can be easily inserted within the recesses 74 of the rear housing 14 for shipping or just prior to sliding the lock members 68 into the receiving members 66 at the initial stage of cassette assembly.

The cover 16 additionally contains a top lip feature 110 around the upper perimeter of the side walls 96 and front wall 94, similar to the upper lip 82 of the rear housing 14. A front groove 112 within the lip 110 provides an area into which the pressure plate 12 will ultimately reside when the cassette 10 is assembled. Further, an upwardly projecting notched flange 114 extends from the lip 110 and is shaped to fit against the interior front surface 116 of the pressure plate 12. The notches 118 are shaped to allow for webbed supports 120 of the pressure plate 12. The upper lip 110 of the cover 16 also contains two slotted apertures 122 within the groove 112 in which the front two snaps 32A of the pressure plate 12 may be inserted into place when the cassette 10 is assembled.

The exterior of the cover 12 contains a series of semicircular ridge shaped protrusions 124 along the sides of the cover which define ridges on the exterior face 94 of the cassette 10. These ridges 124 allow for ease of handling and gripping the cassette 10. Also, the sides of the cassette 10 also contain raised alignment projections 126. The alignment projections 126 aid in aligning the cover and rear housing 14 during assembly. Specifically when the cover 16 and its lock members 68 are placed within the recesses of the rear housing 14 the alignment projection 126A on the cover is aligned with the lower alignment projection 126B on the rear housing. When the cover 16 is moved into the locked position the projection 126A will align with projection 126C on the rear housing. Additionally, these alignment projections provide for convenient cassette handling and mounting. Moreover, the cover 12 has an arched surface to allow for slightly greater reservoir volume within the cassette 10. The outer lower faces of the cover 16 and rear housing 14 contain projecting surfaces 128 that provide a level surface upon which the cassette 10 is able to rest if placed on a flat surface. The projecting surfaces 128 thereby account for and adjust the otherwise slightly angled lower surface of the cassette 10.

As described above, the pressure plate 12 and rear housing 14 are typically preassembled with the four snaps 32B and 32C at manufacture. Further, at the time of manufacture, an empty medication bag is placed within the open interior chamber 64 of the rear housing 14 cassette area. A tube attached to the bag is threaded through the upper opening 130 of the pressure plate 12 and across the pressure plate passageway 26. Next, the cover 16 is placed into the rear housing 14 such that the six lock members 68 of the cover 16 reside within the recesses 74 of the rear housing 14 but without sliding the cover 16 into the receiving members 66 and corresponding locked position. The assembly remains in this position during sterilization and transit to a pharmacist or other customer.

Upon receipt, the customer typically undertakes a number of steps to fill the medication reservoir with the prescribed drug. This can be done by hand or with use of a mediation pump. Importantly, in this design the cover 16 can be removed and access to the touch and manipulate the medication bag remains possible at this stage. This access can be especially useful if manipulating the medication bag to remove air bubbles and the like is desired. This type of access was not previously made possible in many cassette designs in which a single piece housing was ultrasonically sealed at manufacture.

When filled by hand, the medication bag is first accessed by sliding the cassette cover 16 down, pulling it away from the rear assembly 92, and setting it aside. A syringe is filled with a desired volume of medication or diluents and is attached to a luer found on the end of the tubing extending from the medication bag. The syringe is emptied to fill the medication bag inside the cassette. After injecting all the material into the bag, the medication bag is massaged by the pharmacist to ensure proper mixing of the medication and to remove air bubbles. Specifically, the bag is squeezed to expand the seams and to rotate large bubbles along the seam to collect smaller air bubbles. Next, the collected large air bubbles are aspirated with a syringe. The tubing is clamped, the syringe is removed, and the medication bag is reinserted into the rear housing 14. Once the medication bag is in place, the cassette 10 is ready to be assembled and locked into a single cassette structure.

The cassette 10 is assembled by aligning the locking members 68 of the cover 16 with the recesses 74 of the rear assembly 92 and placing the two pieces together. Next, a user grasps the rim of the pressure plate 12 with both hands and pushes downwardly against a hard surface until the cover 16 clicks into place and the markings on the cover are properly aligned. Accordingly, no tools are required to assemble the medication cassette 10.

The features of the cassette and locking arrangement of two piece cassette assembly are set forth in greater detail in FIGS. 7, 8, and 9A-C. FIG. 7 first discloses the two pieces of the two piece cassette set forth in an exploded assembly view. The two pieces generally representing the first assembly 92 and second assembly 93. The cassette is typically manufactured into these two pieces such that no tools or equipment is required by an individual seeking to snap together and secure the cassette 10. For better illustration, an empty medication bag is absent from FIG. 7 which would generally be located in the central chamber 64 of the rear assembly 92 with attached tubing passing through opening 130 in the pressure plate 12 and across its surface. Typically this medication bag would be in place when the device is shipped or filled with medication prior to closure.

Figure 8:
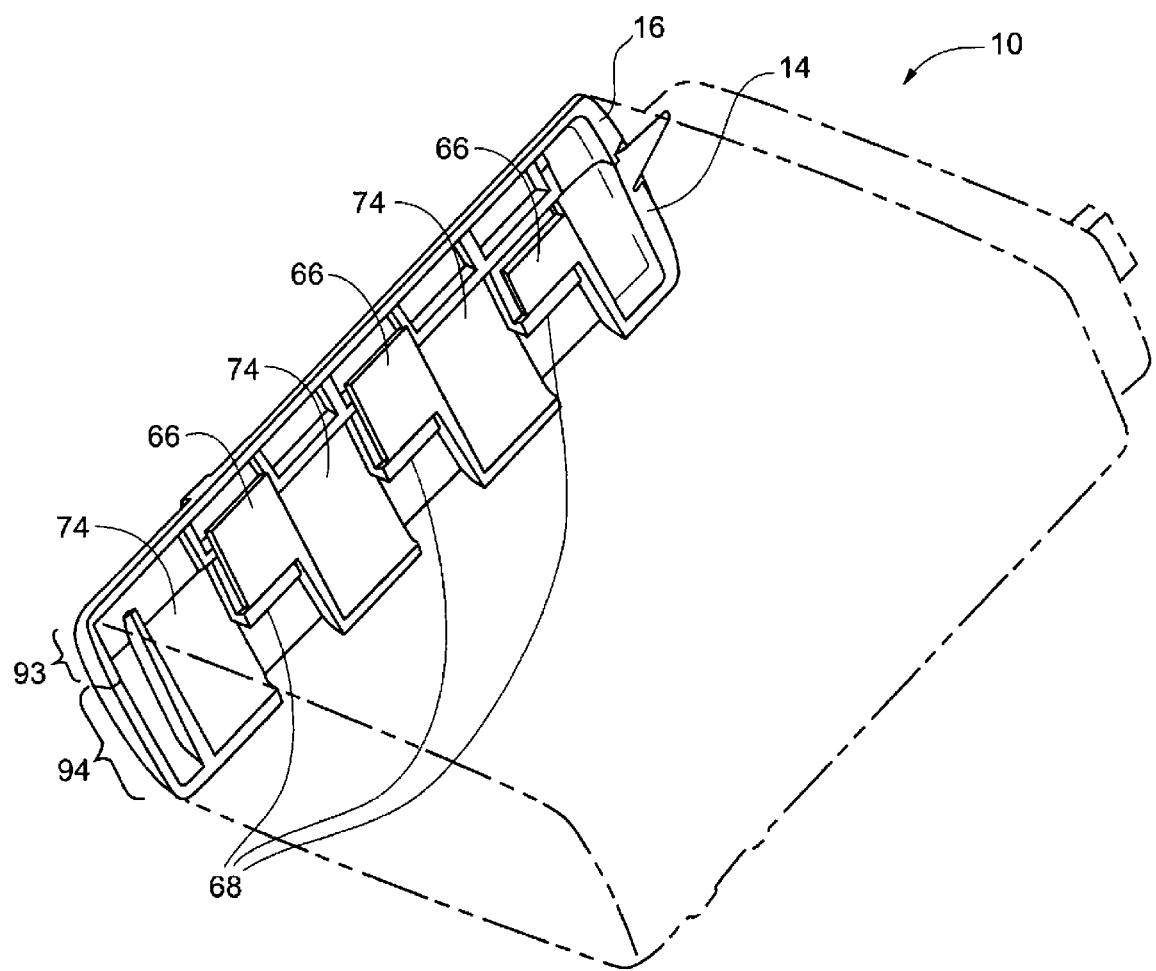
FIG. 8 illustrates generally a partial perspective view of a medication cassette including a partial cross-section of the locking arrangement on one side of the cassette, according to an embodiment of the invention.

FIG. 8 sets forth a cross sectional view of one side of an assembled cassette 10 such that the structure and operation of the lock features can be better understood and illustrated. In this view, the adjacent and overlapping features of the cover 16 and rear assembly 92 are seen. Specifically, the three receiving members 66 of the rear assembly 92 can be partially seen. Also three recesses 66 of that side of the rear assembly 92 can be identified. Further, three lock members 68 of the cover 16 are shown. The locking arrangement along the opposite side of the assembled cassette 10 (not shown in FIG. 8) is generally a mirror image of the cross section shown. The opposite side locking arrangement works in cooperation with and in generally the same manner as the one shown and discussed in FIGS. 8 and 9A-C.

Figure 9A:
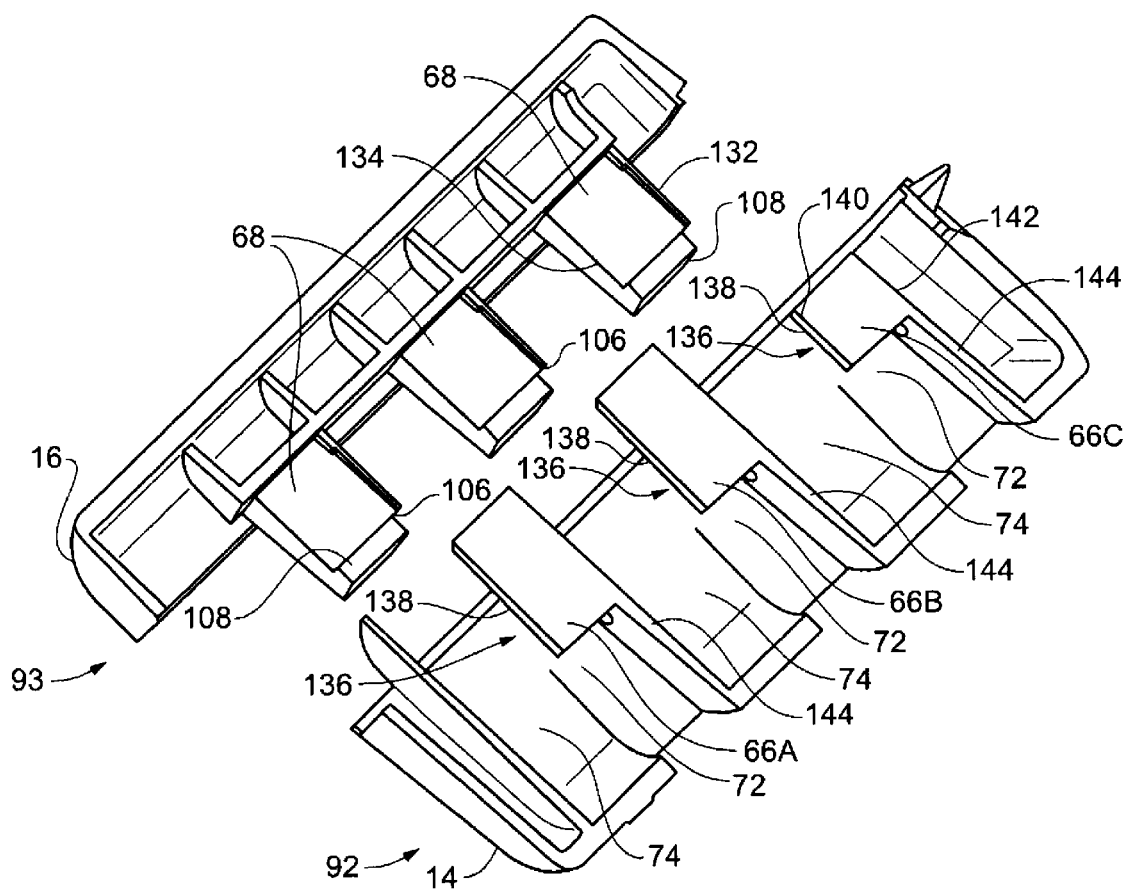
FIG. 9A illustrates generally a partial cross-sectional view similar to the view shown in FIG. 8 but where the locking components of a medication cassette are in a separated position, according to an embodiment of the invention.
Figure 9B:
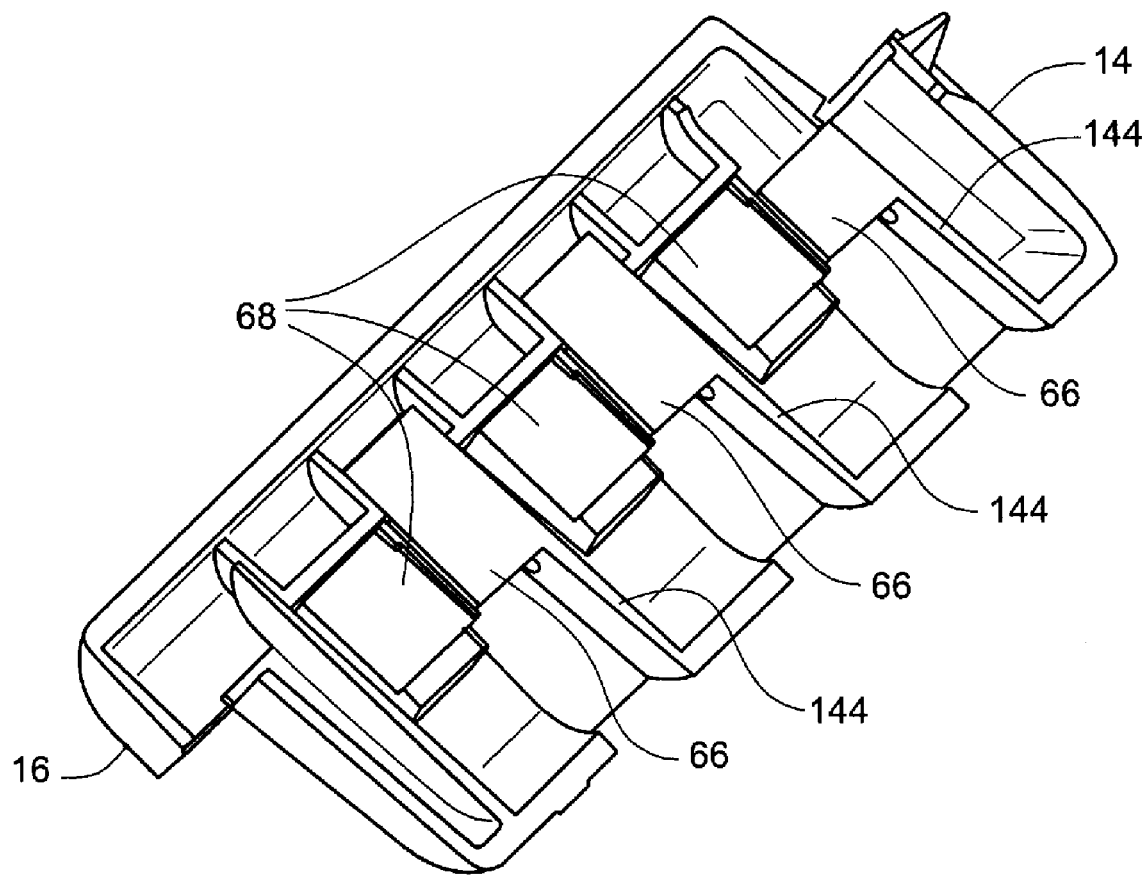
FIG. 9B illustrates generally a partial cross-sectional view similar to the view shown in FIG. 8 but where the locking components of a medication cassette are in the initial assembly position, according to an embodiment of the invention.
Figure 9C:
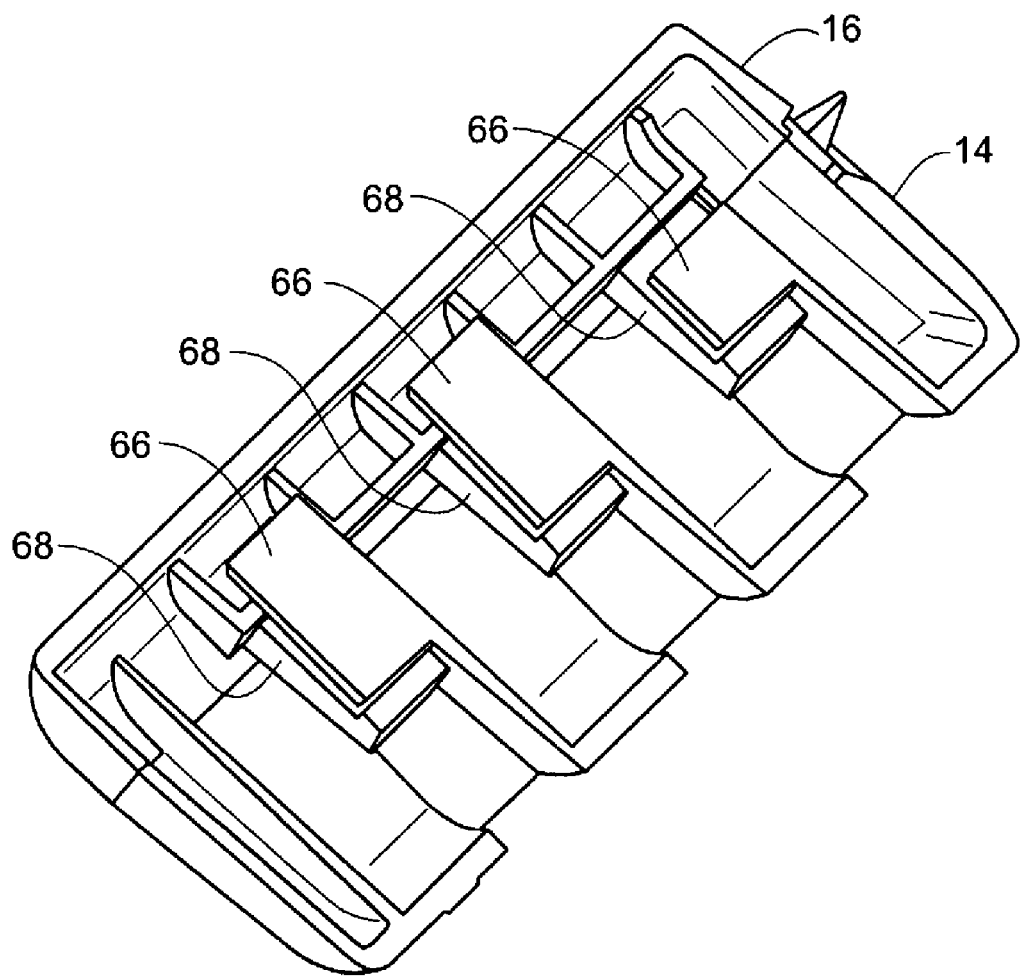
FIG. 9C illustrates generally a partial cross-sectional view similar to the view shown in FIG. 8 where the locking components of a medication cassette are in the locked position, according to an embodiment of the invention.

FIGS. 9A-C are intend to illustrate three configurations of the cover 16 and rear assembly 14 for cross sectional views taken at similar locations to the one shown in FIG. 8 and are taken of these components at different stages of cassette assembly. FIG. 9A first sets forth the components of the cover 16 and rear assembly 92 before they are assembled together, such that the features that are part of the cover 16 or rear assembly 92 can be readily identified.

The cover 16 components shown include three lock member protrusions 68. The inside angled interior surfaces 104 are facing upward in FIG. 9A. In general, the angled interior surface 64 of each lock member 68 slopes upward from the thinnest lock feature cross section on the top edge 132 of each lock member 68 to the thickest cross sectional section of the lock feature on the lower edge 134 of each lock member 68. The flat surfaces 102 are found on the opposite side of the lock member 68 although these cannot be seen from this viewpoint. Undercut tab bars 108 are found on the ends of each of the lock member 68. While these tab bars 108 are of the same general shape as the rest of the lock member 68, the tab bars 108 are slightly shorter than the width of the lock member 68 giving the appearance of a notch 106 found in the corner of each lock member 68. Further, the tab bars 108 are wider than the thickness of the rest of the lock member 68 causing a rectangular bar to project outward at the end of the lock members 68.

The rear assembly 92 includes three receiving members 66. Each of these receiving members 66 project outwardly in a generally spaced apart manner. A gap 136 exists between each of these receiving members 66 and the outer housing wall 54 located directly underneath the receiving members seen in FIG. 9A. Accordingly, these gaps 136 enable components to be wedged between those two surfaces. Furthermore, the downward facing surface 138 of these receiving members has a sloped face, not readily seen in FIG. 9A. However, the face 138 can be understood as sloping from the narrowest cross section of the receiving feature 66 at lower edge 140 to the thickest cross section at top edge 142. It can be seen that the two lower receiving members 66A and 66B are slightly longer than the top receiving member 66C. The extra length on the end of each of recovery members 66A and 66B sections does not have a sloped surface and exists largely to aid in the proper alignment of the cover 16 and rear assembly 92. Recesses 74 are shown in the rear assembly 92 between each of the receiving members 66. These recesses 74 generally provide open pockets of space, located around the interior perimeter of the rear assembly 92.

FIG. 9B generally illustrates the configuration of the cassette when the cover 16 is initially removeably placed in the rear assembly 92 during assembly. This configuration may also be the configuration that is used when the cassette assembly is shipped to the customer or pharmacist. As shown, the lock members 68 are placed within the recesses of the rear assembly as far as they are permitted to extend. In this configuration the outer perimeter edge of the cover 16 and the perimeter edge of the rear assembly 92 are fully engaged. At this point the cover 16 and rear assembly 92 is loosely fitted together, and pulling these members apart could be readily done by a user.

FIG. 9C sets forth the locked configuration of the cassette 10. To achieve this position, the cover 16 and rear assembly 92 were first placed together into the configuration of FIG. 9B, and then slid laterally such that the locking members 68 slide underneath the receiving members 66. The two pieces are slid as far as possible as the tab bars 108 prevent further movement in this direction due to the obstructing intermediate flange supports 144. Additionally, a snug fit between these pieces is provided and further movement is prevented due to the sloped surfaces of the locking members 68 and receiving members 66 sliding up the inclined surfaces of each other. Here, the wedged surfaces generally serve as shims for bringing the pieces together into close contact. Although it cannot be seen from the view of FIG. 9C, when the two members have been slid fully into this configuration, this also necessitates that the two snaps 32A found in the front of the pressure plate 12 are slid into the slotted apertures 122 of the cover 16. Once these snaps 32A are secured into place, the cover 16 and rear assembly 92 can no longer be slid laterally with respect to one another. Accordingly, a secured housing is provided which cannot easily be opened without substantial deformation or damage to the housing and locking structures.

The embodiments above are intended to be illustrative and not limiting. For example, the number of locking members, receiving members, tabbed snaps and slotted apertures may vary in some embodiments as well as the size of the enclosed medication reservoir. Additional embodiments are within the claims. Although the present invention has been described with reference to particular embodiments, workers skilled in the art will recognize that changes may be made in form and detail without departing from the spirit and scope of the invention.

Various modifications to the invention may be apparent to one of skill in the art upon reading this disclosure. For example, persons of ordinary skill in the relevant art will recognize that the various features described for the different embodiments of the invention can be suitably combined, un-combined, and re-combined with other features, alone, or in different combinations, within the spirit of the invention. Likewise, the various features described above should all be regarded as example embodiments, rather than limitations to the scope or spirit of the invention. Therefore, the above is not contemplated to limit the scope of the present invention.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. A disposable medical cassette for housing medication in a tamper resistant enclosure for selective coupled attachment to an ambulatory infusion pump, comprising:
    a first assembly comprising a rear housing and a pressure plate, said first assembly including a plurality of tamper resistant lock receiving structures formed in the rear housing and at least one tabbed snap member, each lock receiving structure having a sloped shim surface and defining an undercut space; and
    a second assembly comprising a cover including a plurality of lock feature protrusions and at least one slotted aperture, each lock feature protrusion having a sloped shim surface and a tab body;
    wherein said first assembly and said second assembly are adapted for permanent coupling by a bifurcated lock system including a first lock arrangement and a second lock arrangement,
        said first lock arrangement defined by said sloped shim surfaces of said lock feature protrusions of the second assembly in a friction and interference fit against said sloped shim surfaces of said lock receiving structures of the first assembly, the friction and interference fit of said sloped shim surfaces drawing the first assembly and the second assembly together into close contact when assembled to form a tight perimeter seam between the first assembly and second assembly, the first lock arrangement further defined by an interference fit of said tab bodies located in said undercut spaces that restricts lateral sliding movement and transverse separating movement of the first and second assemblies, said second lock arrangement defined by said at least one tabbed snap member of the first assembly engaged within said at least one corresponding slotted aperture of the second assembly such that the second lock arrangement cannot be accessed to reopen the cassette without compromising the cassette once assembled.

2. The disposable medical cassette of claim 1, wherein the pressure plate comprises polycarbonate.

3. The disposable medical cassette of claim 1, wherein the cover comprises polypropylene.

4. The disposable medical cassette of claim 1, wherein the first assembly has at least six of said tamper resistant lock receiving structures.

5. The disposable medical cassette of claim 1, wherein pressure plate contains a latch arch, a pair of attachment hooks, a plurality of tubing guide members, and a plurality of tabbed snap members.

6. The disposable medical cassette of claim 1, wherein the first assembly has a set of interior walls and a set of exterior walls.

7. A disposable medical cassette for housing medication in a tamper resistant enclosure for selective coupled attachment to an ambulatory infusion pump, comprising:
  a cover member having a perimeter adapted for coupling and including a plurality of lock members with sloped engagement surfaces; and
  a rear assembly comprising a top pressure plate and a partial housing structure having a set of outer walls disposed about the sides and bottom of the structure, each wall of said set of outer walls including two opposing planar surfaces, and a set of inner walls disposed within the outer walls and mirroring the general orientation of the outer walls, each wall of said set of inner walls including two opposing planar surfaces, the outer walls defining a perimeter for coupled engagement to the perimeter of the cover member;
  wherein the inner walls have greater height than the outer walls to provide a barrier that obstructs direct access to a central chamber of the cassette via any seam formed between the perimeter of the cover member and the perimeter of the rear assembly when in coupled engagement; and
  wherein a plurality of receiving members containing sloped engagement surfaces are integrally formed in the rear assembly between the outer walls and the inner walls, said sloped engagement surfaces of the plurality of receiving members providing a friction and interference fit with said sloped engagement surfaces of the plurality of lock members constituting a shim arrangement for drawing the cover member into close contact with the rear assembly when assembled to form a tight perimeter seam between the cover member and the rear assembly.

8. The disposable medical cassette of claim 7, wherein the top pressure plate comprises polycarbonate.

9. The disposable medical cassette of claim 7, wherein the cover comprises polypropylene.

10. The disposable medical cassette of claim 7, wherein the cover member and rear assembly are coupled by at least one pair of tabs and apertures and at least one pair of lock members and receiving members.

11. The disposable medical cassette of claim 10, wherein the cover member has six lock members.

12. The disposable medical cassette of claim 11, wherein the rear assembly has six receiving members.

13. The disposable medical cassette of claim 7, wherein the rear assembly has a central chamber with an interior volume larger than 250 cubic centimeters.

14. A disposable medical cassette for coupled attachment to an ambulatory infusion pump for housing medication, comprising:
  a multi-piece assembly comprising two interlocking pieces designed for tool-less manual assembly to securely house a reservoir of medication;
  wherein the disposable medical cassette has a tamper resistant configuration having multiple types of locking assemblies, including
    at least one snap and aperture lock assembly, including one or more snaps, for holding the two interlocking pieces together to prevent lateral sliding movement of the interlocking pieces with respect to one another, and
    at least one additional lock assembly including a plurality of lock feature protrusions with a first set of sloped shim surfaces and a plurality of corresponding lock receiving structures with a corresponding second set of sloped shim surfaces to prevent sliding and separating movement of the two interlocking pieces when assembled, said first and second sets of sloped shim surfaces having providing a friction and interference fit with each other for drawing the two interlocking pieces into close contact to form a tight perimeter seam between the two interlocking pieces when assembled,
  wherein an outside surface of the cassette obscures direct access to the snap and aperture lock assemblies such that said one or more snaps may not be readily deflected and released from engagement once assembled;
  wherein the assembled disposable medical cassette provides an interior chamber for housing the reservoir of medication.

15. The disposable medical cassette of claim 14, wherein the interior chamber has a volume of at least 250 cubic centimeters.

16. The disposable medical cassette of claim 15, wherein at least one of the interlocking pieces comprises polypropylene.

17. The disposable medical cassette of claim 14, wherein the cassette includes a pressure plate having attachment hooks and a latch arch projecting from a top surface and having a plurality of snaps for attachment projecting from a bottom surface.

18. A method for assembling a medication cassette, comprising:
  obtaining a first assembly and a second assembly adapted for permanent coupling and housing a medication reservoir for an ambulatory infusion pump, the first assembly including a pressure plate and rear housing having tabbed snaps projecting from the pressure plate in a direction perpendicular to the top surface of the pressure plate and a plurality of receiving members located along the sides of the rear housing such that the receiving members are spaced apart by a plurality of recesses, the second assembly comprising a cover including a plurality of slotted apertures and a plurality of lock members that protrude from the cover in a direction generally perpendicular to the face of the cover;
  filling a medication bag;
  placing the medication bag within the first assembly;
  placing the lock members of the second assembly into spaced apart recesses of the first assembly;
  sliding the lock members of the second assembly into the receiving members of the first assembly while engaging the tabbed snaps of the first assembly into the slotted apertures of the second assembly; and securing the first and second assemblies such that the tabbed snaps are not accessible without compromising the cassette.

19. A method for assembling a medication cassette, comprising:

providing instructions for medication cassette assembly, including:

obtaining a first assembly and a second assembly adapted for permanent coupling and housing a medication reservoir for an ambulatory infusion pump, the first assembly including a pressure plate and rear housing having tabbed snaps projecting from the pressure plate in a direction perpendicular to the top surface of the pressure plate and a plurality of receiving members located along the sides of the rear housing such that the receiving members are spaced apart by a plurality of recesses, the second assembly comprising a cover including a plurality of slotted apertures and a plurality of lock members that protrude from the cover in a direction generally perpendicular to the face of the cover;

filling a medication bag;

placing the medication bag within the first assembly;

placing the lock members of the second assembly into spaced apart recesses of the first assembly;

sliding the lock members of the second assembly into the receiving members of the first assembly while engaging the tabbed snaps of the first assembly into the slotted apertures of the second assembly; and securing the first and second assemblies such that the tabbed snaps are not accessible without compromising the cassette.

* * * * *